US006633377B1

(12) United States Patent
Weiss et al.

(10) Patent No.: US 6,633,377 B1
(45) Date of Patent: Oct. 14, 2003

(54) DARK VIEW INSPECTION SYSTEM FOR TRANSPARENT MEDIA

(75) Inventors: Adam Weiss, Pickering (CA); Alexandre Obotnine, Willowdale (CA)

(73) Assignee: Image Processing Systems Inc., Ontario (CA)

( * ) Notice: Subject to any disclaimer, the term of this patent is extended or adjusted under 35 U.S.C. 154(b) by 0 days.

(21) Appl. No.: 09/553,216

(22) Filed: Apr. 20, 2000

(51) Int. Cl.⁷ .............................................. G01N 21/89
(52) U.S. Cl. .................................... 356/239.1; 356/430
(58) Field of Search ........................... 356/239.1, 239.2, 356/239.3, 239.4, 239.5, 239.6, 239.7, 239.8, 429, 430, 431

(56) References Cited

U.S. PATENT DOCUMENTS

| | | | |
|---|---|---|---|
| 3,533,706 A | * 10/1970 | Maltby et al. | 356/239.1 |
| 3,737,665 A | 6/1973 | Nagae | |
| 4,492,477 A | 1/1985 | Leser | |
| 4,500,203 A | * 2/1985 | Bieringer | 356/239.4 |
| 4,583,854 A | 4/1986 | Lozar | |
| 4,641,966 A | 2/1987 | Lemmers et al. | |
| 4,943,713 A | * 7/1990 | Yoshida | 356/239.5 |
| 5,220,178 A | * 6/1993 | Dreiling et al. | 356/430 |
| 5,459,330 A | 10/1995 | Venaille et al. | |
| 6,011,620 A | 1/2000 | Sites et al. | |

FOREIGN PATENT DOCUMENTS

| | | |
|---|---|---|
| CA | 2252308 | 10/1998 |
| DE | 3926349 A1 | 8/1989 |
| DE | 41 39 094 | 11/1991 |
| DE | 198 09 505 | 3/1998 |
| EP | 0 317 638 | 5/1989 |
| EP | 0 559 916 | 9/1992 |
| GB | 1 526 930 | 12/1974 |
| WO | WO 96/05503 | 2/1996 |
| WO | WO 00/26647 | 5/2000 |

OTHER PUBLICATIONS

Patent Abstracts of Japan, vol. 1997, No. 04, Apr. 30, 1997, for: JP 08 327561 A, Dec. 13, 1996.

Patent Abstracts of Japan, vol. 016, No. 468, Sep. 29, 1992, for: JP 04 168351, Jun. 16, 1992.

Patent Abstracts of Japan, vol. 1996, No. 11, Nov. 29, 1996, for: JP 08 193955, Jul. 30, 1996.

* cited by examiner

Primary Examiner—Richard A. Rosenberger
(74) Attorney, Agent, or Firm—Merchant & Gould P.C.

(57) ABSTRACT

Apparatus and a method for the detection and identification of light diverting and transparent defects with optical properties in a transparent medium. The apparatus has a light source with an aperture stop, a lens system focusing an image of the aperture stop at a plane, and means to pass the transparent medium through said column of light. The apparatus and method provide dark view images of the defects. The apparatus and method may be combined with a viewing area inspection system. The transparent medium may be curved, and especially face plates for cathode ray tubes.

57 Claims, 4 Drawing Sheets

DARK VIEW INSPECTION SYSTEM FOR TRANSPARENT MEDIA

FIELD OF THE INVENTION

The present invention relates to a non-contact inspection system for detection and identification of the type of defects in transparent media, including flat glass and moulded curved glass e.g. glass of cathode ray tube (CRT) face plates, plastic sheets, lens blanks and the like. The system is intended to operate on a continuous production line at line speed, and for the identification of a wide variety of types of defects, including bubbles, scratches, chips, cracks and other optical defects. The system is a dark view inspection system for detection and identification of light diverting and transparent defects with optical properties in transparent media.

BACKGROUND OF THE INVENTION

In processes for manufacture of transparent media, it is necessary to be able to inspect the transparent media for defects. Such defects may be in the form of scratches, bubbles, chips, blemishes and a wide variety of other defects. However, the mere detection of defects is insufficient in that the manufacturer of the transparent media needs to know whether the defects are insignificant e.g. minor in nature and thus acceptable to the customer, or major flaws such the transparent media would not conform to specifications established by the customer.

It is possible to use human visual inspection of transparent media and to identify those articles of transparent media that have defects. In addition, using visual inspection, it is possible to identify the location and possibly the type of defect. However, human visual inspection is not acceptable because of the time and cost involved in conducting a visual inspection, and the limitations of such a method. It would be preferable to be able to conduct the inspection on-line in the production process, at production speeds, so that defects could be rapidly identified and communicated to production personnel and/or the articles of transparent media with the defects could be readily and quickly separated from articles meeting quality specifications in an effective manner.

Methods have been developed for the inspection of sheets of glass using optical techniques that involve use of lasers. While lasers can be very effective in the detection of defects in flat or essentially flat sheets of glass, imaging optics for laser light require a small f-stop i.e. a large aperture, and consequently the depth of field is small. This limits the usefulness of laser light, especially in circumstances where the glass or article has curvature. One example of such a curved article is the face plate of a cathode ray tube (CRT), which requires good optical properties. Focusing on the surface of a curved article to detect defects is difficult if the depth of field of the imaging optics is small.

SUMMARY OF THE INVENTION

Apparatus and a method have now been found that is particularly intended for use in inspection of curved articles of transparent media in a production line, at production speeds, in a manner that shows the magnitude, type and location of the defects in the transparent media.

Accordingly, one aspect of the present invention provides an apparatus for the detection and identification of light diverting and transparent defects with optical properties in a transparent medium, comprising:

a) a light source of extended length and width;
b) a lens system to form a column of light from said light source and to focus said light at a plane;
c) an optical recording device located at said plane;
d) an aperture stop located at said source of light, said lens system focusing an image of said aperture stop at said plane, said optical recording device being located at said image; and
e) means to pass said transparent medium through said column of light.

Another aspect of the present invention provides a method for detection and identification of light diverting and transparent defects with optical properties in a transparent medium, comprising:

a) passing said transparent medium through a column of light from a source of light having an aperture stop therein;
b) focusing said column of light at a plane, an image of said aperture stop being focused at said plane, said plane having an optical recording device at said image of said aperture stop; and
c) recording light from a light diverting and transparent defect with optical properties in said transparent medium with said optical recording device.

A further aspect of the present invention provides a method for the detection and identification of light diverting and transparent defects with optical properties in a transparent medium, comprising:

a) passing light through a transparent medium;
b) providing an aperture stop in said light, and focusing said aperture stop at an optical recording device;
c) measuring intensity of light diverted by a light diverting and transparent defect with optical properties in said transparent medium using said optical recording device.

Another aspect of the present invention provides apparatus for the detection of defects in a transparent medium, comprising:

a) a viewing area inspection system for the transparent medium;
b) a dark view inspection system for the transparent medium; and
c) means to pass said transparent medium through said viewing area inspection system and said dark view inspection system, in sequence.

Yet another aspect of the present invention provides apparatus for the detection and identification of light diverting and transparent defects with optical properties in a transparent medium, comprising:

a) first and second light sources of extended length and width, each light source providing a column of light;
b) a first optical recording device associated with the first light source and a second optical recording device associated with the second light source;
c) means to pass said transparent medium through said columns of light;
d) said second light source having an aperture stop and a lens system to form a column of light from said light source and to focus said light at a plane, a lens system focusing an image of said aperture stop at said plane, said second optical recording device being located at said image.

A further aspect of the present invention provides a method for the detection and identification of defects in a transparent medium, comprising:

a) passing said transparent medium through first and second light sources of extended length and width, each light source providing a column of light;

b) focusing the column of light from the first light source at a first optical recording device and focusing the column of light from the second light source at a second optical recording device;

c) recording images of said transparent medium at said first and second optical recording devices; and d) combining said images for detection and identification of the defects.

BRIEF DESCRIPTION OF THE DRAWINGS

The present invention is illustrated by the embodiments shown in the drawings, in which.

DETAILED DESCRIPTION OF THE INVENTION

Figure 1:
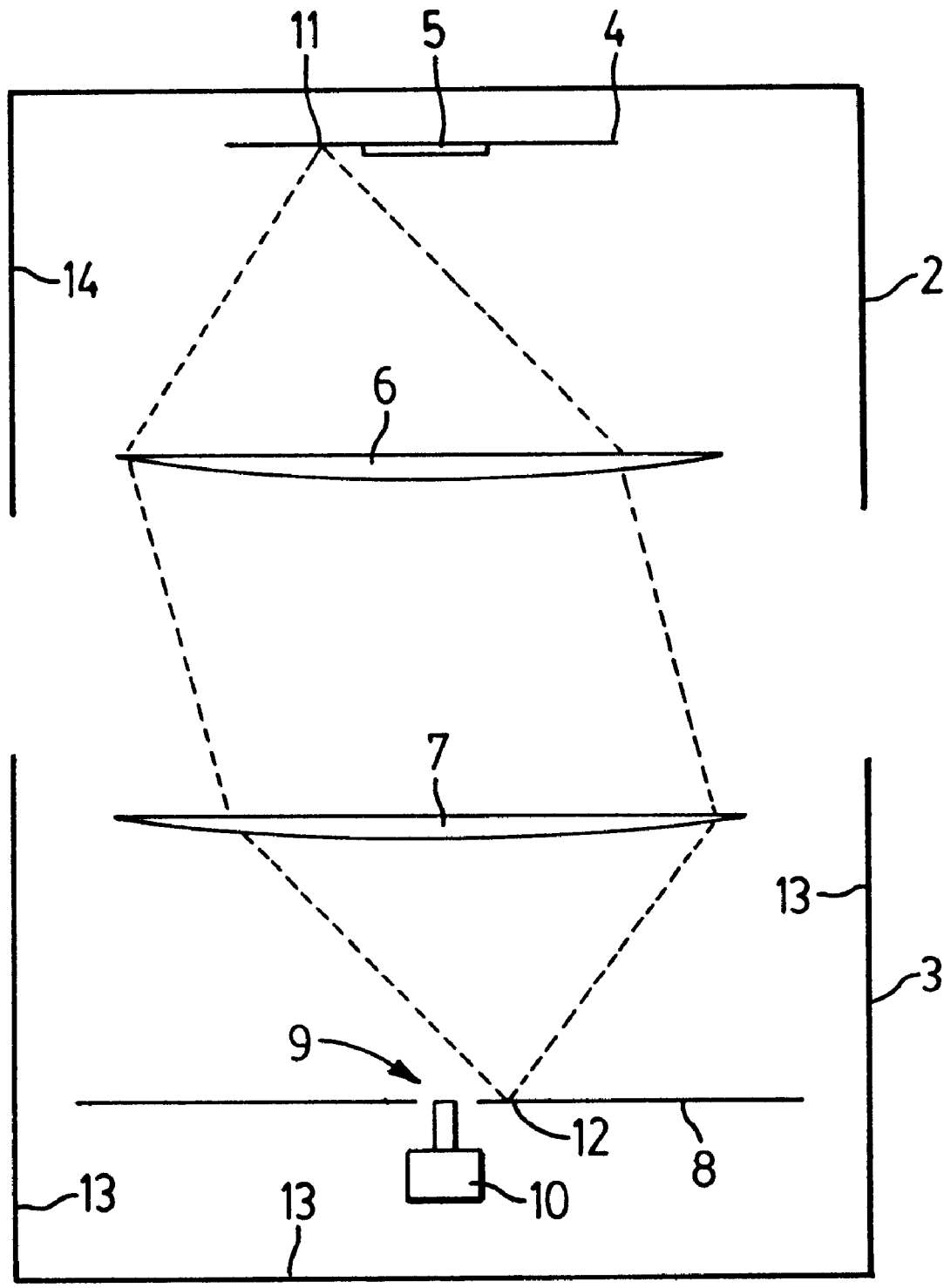
FIG. 1 is a schematic representation of an end view of the dark view glass inspection apparatus in accordance with the present invention.

The present invention is directed to inspection of a variety of types of transparent media for optical defects. Examples of the types of transparent media include both glass and plastics. The glass may be, for instance, flat sheets of glass, e.g. float glass and tempered glass, formed sheets of glass e.g. curved glass, laminated glass such as windshields and molded glass such as cathode ray tube (CRT) and lens blanks. The plastic may be molded plastic e.g. ophthalmic lens blanks and other curved structures as well as curved and flat transparent sheets of plastics. The invention may also be used for the inspection of other curved or flat transparent media.

Techniques for the manufacture of glass are known. For example, glass may be converted to a molten state and then cast into a mould or onto molten tin metal so that glass with a smooth surface may be obtained. Nonetheless, the glass that has been cast may be subject to a number of defects, including the presence of bubbles, dirt, stones, tin-drip distortion and other defects. Some such defects might arise from raw materials fed to the process while other defects will arise from processing problems, including incorrect temperature or other process parameters and ageing of apparatus, especially of kilns or other apparatus used in the heating of the glass.

Subsequent to the casting and any cutting of the glass, the glass is transferred to a manufacturer of glass articles for a particular end-use. In the automobile industry, for instance, the glass articles could be the windows of the vehicle, in which event the manufacturer will shape the glass to a particular size and configuration, prepare ground edges to the glass, cut holes in the glass in locations as required, imprint logos or other writing in the glass and otherwise process the cut glass to a predetermined set of specifications. Despite care in operation of the process, the various steps can result in the formation of chips, cracks, scratches, and other defects that might render the glass unacceptable to a customer. The manufacturer must be able to detect the defects, and separate sheets of glass conforming to specification from those that do not. In other embodiments, the glass is flat sheet intended for end-uses other than the automobile industry.

Examples of some of the defects that may be present in a sheet of glass include bubbles i.e. inclusion of gas in the glass in a generally spherical shape, blisters i.e. elongated bubbles, seeds i.e. minute bubbles, dirt, lint, shell chips i.e. small pieces of glass broken away from the main body of the glass, stones, strands i.e. very fine, string-like pieces of foreign matter embedded in the glass or laminates thereof, vents i.e. small cracks usually appearing at the corners of cut glass, pits or digs i.e. small hollows and other defects.

Alternatively, the glass may be curved or formed glass. Such curved glass might be intended for the automobile industry, but it could be intended for other end-uses. For instance, the glass could be the face plate of a cathode ray tube (CRT) for a television or a computer. Such glass is normally cast into a mould. All such glass must meet the particular specifications for the manufacturer of articles from the glass, and ultimately meet the requirements of the end-user e.g. the purchaser of the television or computer. Examples of defects that may occur in curved glass e.g. CRT glass, include scratches, pits i.e. open blisters, elongated blisters, cords or viscous strings, cold glass, stones and thermal pressure defects.

It is to be understood that in some instances the glass may be in the form of a laminated or tempered glass or other glass, to give it strength, shatter resistance or other properties. The processes used to form such glass may add to the potential defects in the sheet of glass.

Although the sheet or article has been described above with respect to glass, the sheet or article may be formed from a transparent plastic, or other transparent media, rather than glass. The defects in the transparent plastic or other transparent media might be the same as found in glass or different e.g. defects arising from the manufacture of the plastic composition that is used and the subsequent processing into an article. The latter defects include gel, dirt, bubbles, stress lines, surface phenomena and the like.

The system of the present invention provides for detection and identification of light diverting and transparent defects with optical properties. The detection and identification may include measurement of the defect, e.g. at least the relative size thereof.

FIG. 1 shows an end view of a dark view glass inspection apparatus in accordance with the present invention, generally indicated by 1. As illustrated in FIG. 1, apparatus 1 has upper housing 2 and lower housing 3. Upper housing 2 has extended light source 4. Light source 4 is of a type that may be referred to as distributed illumination. It is not a laser but rather a broad, diffused light source. It may be in the form of a source of light and an opaque sheet to provide an even distribution of light.

Light source 4 has aperture stop 5 in a central location. Aperture stop 5 may be a non-transparent section applied to light source 4, or located juxtaposed to light source 4. The non-transparent section could be paint applied to light source 4, or a metal or other object located at or juxtaposed to light source 4. The form of aperture stop 5 may be varied widely, provided that light is not transmitted through aperture stop 5. The shape may be varied but a circular shape is preferred so as to form a circular or symmetric illumination source. Such a shape does not give preference to any orientation of elongated defects. In particular, the absence of orientation of elongated defects e.g. scratches and elongated bubbles with respect to the orientation of light provides better illumination and detection. If the light was oriented, elongated defects oriented in the direction of travel of the transparent media could be difficult to detect and analyse for shape and size.

Upper housing 2 also has first lens 6 located in the lower part (as viewed) of the housing. Upper housing 2 is open on its lower side. Conversely, lower housing 3 is open on its upper side.

Lower housing 3 has second lens 7 located in the upper part of the housing. In addition, lower housing 3 has plane 8 with aperture 9 therein; it is understood that plane 8 is an image plane, and not a plate or other physical layer, and that aperture 9 indicates the "image" of aperture stop 5 in plane 8. Optical recording device 10, which is a camera and especially a time delayed integration (TDI) device, is located in aperture 9.

First lens 6, which may be a plurality of lenses i.e. a lens system, forms a column of light that passes from first lens 6 to second lens 7. Second lens 7, which may also be a plurality of lenses i.e. a lens system, focuses the light at plane 8. In particular, an image of aperture stop 5 is focused at aperture 9, and hence at camera 10.

The light path of a beam of light from point 11 on light source 4 passes through lenses 6 and 7 and is focused at point 12 at plane 8. Thus, light from a region of light source 4 other than aperture stop 4 is focused away from camera 10.

Inner surface 13 of lower housing 3 is a black light-absorbent surface to prevent reflections that might affect the image obtained by camera 10. Similarly, inner surface 14 of upper housing 2 should also be a black light-absorbent surface.

Figure 2:
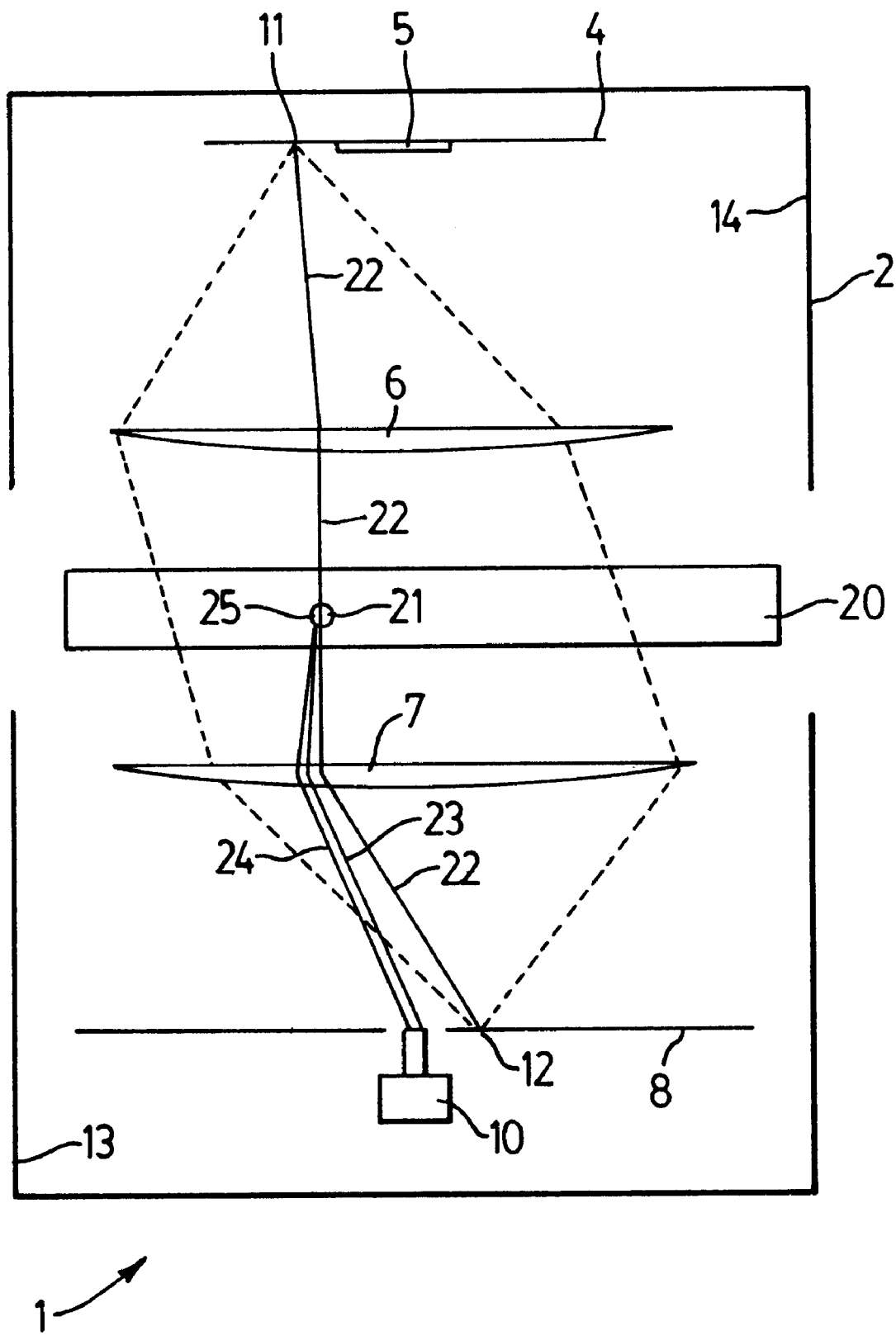
FIG. 2 is a schematic representation of the dark view glass inspection apparatus of FIG. 1, including a transparent medium with a defect.

Upper housing 2 is spaced from lower housing 3, to allow passage of transparent medium 20, as seen in FIG. 2. Transparent medium 20 would be supported by a series of rollers (not shown) so as to transport transparent medium 20 through apparatus 1.

Transparent medium 20 is shown as having a defect 21. While the nature of the defect may vary, as discussed herein, defect 21 is shown in FIG. 2 as being a bubble. In the absence of defect 21, light beam 22 from point 11 would pass through transparent medium 20 and be directed to point 12 on plate 8. Similarly, the image of aperture stop 5 would be at aperture 9, and thus recorded by camera 10 as absence of light. Thus, camera 10 would record a "dark view".

In the presence of defect 21, light beam 22 is diverted e.g. refracted, scattered or diffracted, depending on the nature of defect 21. As shown in FIG. 2, light beam 22 is diverted at least in part as light beams 23 and 24; light beams 23 and 24 are shown as originating at edge 25 of defect 21. Light beams 23 and 24 are focused at camera 10, which records the presence of defect 21 in transparent medium 20. Moreover, the image recorded at camera 10 from light beams 23 and 24 will be characteristic of the type of defect 21 in transparent medium 20. Camera 10 is focussed on the transparent medium 20 and has sufficient depth of field to image any defects over the entire thickness of transparent medium 20.

In operation, as a transparent medium without any defects is passed through apparatus 1, camera 10 would not receive and record any images other than edges of the transparent medium. If the transparent medium has a defect, then an image of the defect would be recorded by camera 10. A line-scan camera should be used, with the images being reconstructed line-by-line. Every line of an image is analyzed on-line to detect regions of interest. Only regions of interest are processed further for analysis of defects, which provides a major reduction in the computer analysis and the capacity of the computer required. If camera 10 is recording continuously or is making multiple images of the transparent medium, then camera 10 would track the passage of the defect through apparatus 1, i.e. the position of the image of the defect at camera 10 would move as transparent medium 20 moves. With information on the edges of the transparent medium, computer software would be able to specify the location of the defect on the transparent medium.

Camera 10 would normally be connected to a computer having software to record and analyze light images received by camera 10, and to compute and/or display the location and type of the defect, as discussed herein.

Figure 3:
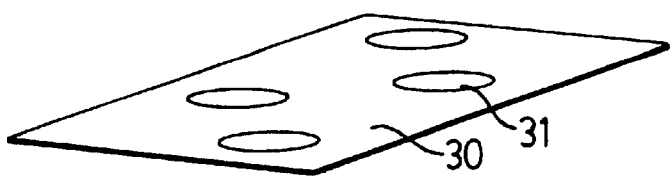
FIG. 3 is a schematic representation of an alternative embodiment of a portion of the dark view glass inspection apparatus of FIG. 1.
Figure 3:
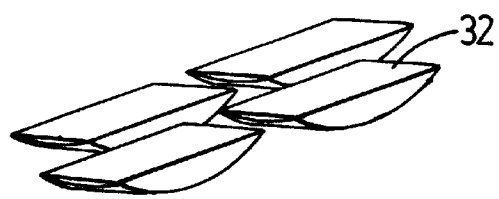
Figure 3:
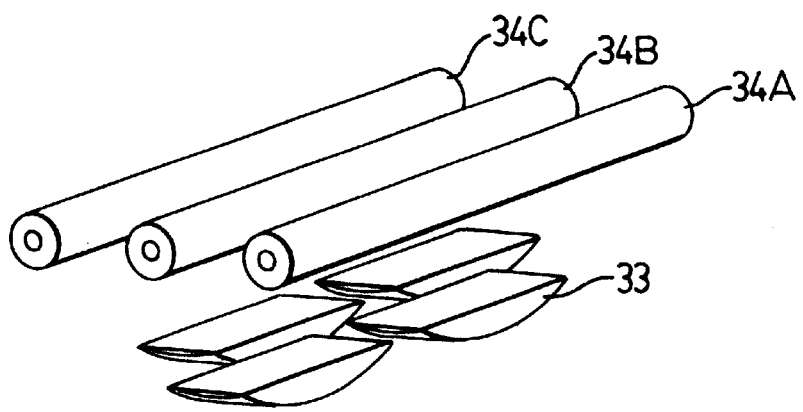
Figure 3:
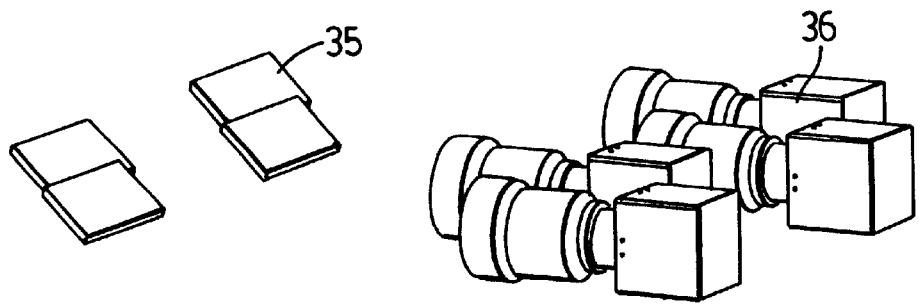

FIG. 3 shows an alternative embodiment of an extended light source 30. Extended light source 30 is shown with four aperture or dark spots 31. The number of dark spots 31 may be varied, but the number needs to be sufficient in a transverse direction in the apparatus to effect coverage of the full width of the transparent medium being inspected. In addition, the number should be sufficient in a machine direction i.e. direction of travel of the transparent medium inspected, to obtain images between at least two sets of successive pairs of rollers to permit adequate tracking of images of a defect.

The apparatus has a set of four lenses 32, which make up the first lens system described above. The number of lenses 32 corresponds to the number of aperture spots 31. A corresponding set of four lenses 33, which correspond to the second lens system described above, are located on the opposed side of rollers 34 from lenses 32. Each lens 33 is aligned with a corresponding lens 32. Moreover, each pair of lenses 32 and 33 are located for optical transmission between for example roller 34A and 34B, or 34B and 34C.

Each pair of lenses 32 and 33 additionally has an associated mirror 35 and camera 36. A mirror corresponding to mirror 35 is not shown in FIGS. 1 or 2, but in the embodiment of FIG. 3, mirror 35 is used to reflect light to cameras 36. Cameras 36 are still located at the equivalent length of light path as camera 10 and aperture 9 described previously i.e. so that images of defects in a transparent medium are focused at camera 36. Use of mirrors 35 and the consequent location of cameras 36 to the side of the apparatus permits a more compact construction, and easier access to cameras 36 for adjustment and attachmnent of controls.

In operation, a transparent medium (not shown) is moved through the apparatus by means of rollers 34A–34C. The transparent medium is illuminated by light source 30. Light from light 30 would normally pass through lenses 32 and 33 and not be reflected by mirrors 35 and not recorded by camera 36. However, if a defect is present, light from light source 30 would be diverted by the defect and a dark view image of the defect would be recorded by cameras 36. The image of the defect would be tracked by cameras 35 as the transparent medium was moved by rollers 34, and the location of the defect in or on the transparent medium could be determined.

The present invention provides a glass inspection system that is capable of automation, and which utilizes optics and a computer vision-based system. The system utilizes a combination of broad illumination techniques, rather than a laser system. The system may be used with a variety of transparent media including glass and plastics.

In preferred embodiments of the invention, the inspection system provides an advanced image analysis with exceptional detection limits, down to 3 µm, as well as the capability to detect and differentiate a wide variety of defects including scratches, bubbles, chips, blemishes and other defects, and identifies the location, type and magnitude of the defects in the transparent medium. The system is capable of being operated at high-speeds e.g. at lines speeds of up to 0.3 m/sec, or higher. In addition, the dark view method of the present invention permits use of a TDI camera, which substantially increases sensitivity and reduces the power requirements for the light source. Thus, the inspection system may be used in-line in many manufacturing processes.

The software used in the system may be featured with a menu-based graphical user interface for ease of use, pass/fail specification changes and new model set ups, as well as automatic change over and calibration of the system.

In a preferred embodiment, a standard user interface screen with a defect map is used, having coloured icons that represent various types of defects. For examples, circles may be used to represent bubbles, squares to represent chips, triangles to represent scratches and so on. The icons may be made to appear at the actual x,y co-ordinates where the defects are located in the sheet of glass. In addition, the icons may be colour coded to represent the size of the defects e.g. the icons could be green to represent a very small defect, yellow to represent a medium defect and red to represent a large defect or reject. Moreover, software may be provided where the user can "click" on any icon to provide characteristics of the defect, including type, size and location. 3-D visualization and mapping of the defects is also possible. Removable surface contaminants such as dust and water, may or may not be not detected by the system, depending on the particular application of the system.

It is to be understood that electronic hardware would be interfaced with the detection system. This hardware would provide for control of the detection system, collection of pixel data from the collection system, compression of the data by relaying for further processing only data that is related to areas of interest in the glass sheet, and for pre-processing of pixel data by applying multi-level thresholds and marking transitions between different levels of intensities. A dedicated Peripheral Process Board (PPB) may be used to further process the data by means of software. The processed data may then be transmitted to a gauge host computer for the purpose of visualization and control, as discussed herein.

The detection system may be set to recognize a threshold of illumination that indicates the presence of defects in the transparent medium. The threshold may be set at levels that represent defects that are unacceptable in the transparent medium being tested, but not recognize defects that would pass specification. All other information e.g. noise or changes in light intensity that do not cause the light intensity to pass through a threshold could be ignored. The transitions that pass through the threshold may be presented on a computer display tube.

The position of the transparent medium within the apparatus is not important, provided that it is located within the width of the light beam. Moreover, the method of the present invention is capable of being used with curved articles of the transparent medium, including CRT face plates. Computer software may be used to more precisely show the location of defects in curved transparent media.

The apparatus is preferably operated with an air pressure slightly above atmospheric pressure so that there is a gentle flow of air outwards from the apparatus, to prevent dust particles being brought into the apparatus. In addition, the air circulated within the apparatus may be passed through at least one HEPA filter, as well as electronic filters, with the air being exchanged frequently e.g. every five minutes. It is important to eliminate dust particles, or at least maintain the dust particles at a minimum, as the lenses are normally within the depth of field of the camera, and dust particles on the lenses will be recognized and interpreted as defects.

Time delayed integration techniques may be used in the detection and analysis of the images that are formed and detected.

The dark view inspection system described herein may be used in association with a viewing area inspection system. Such a combination of systems is shown in FIG. 4.

Figure 4:
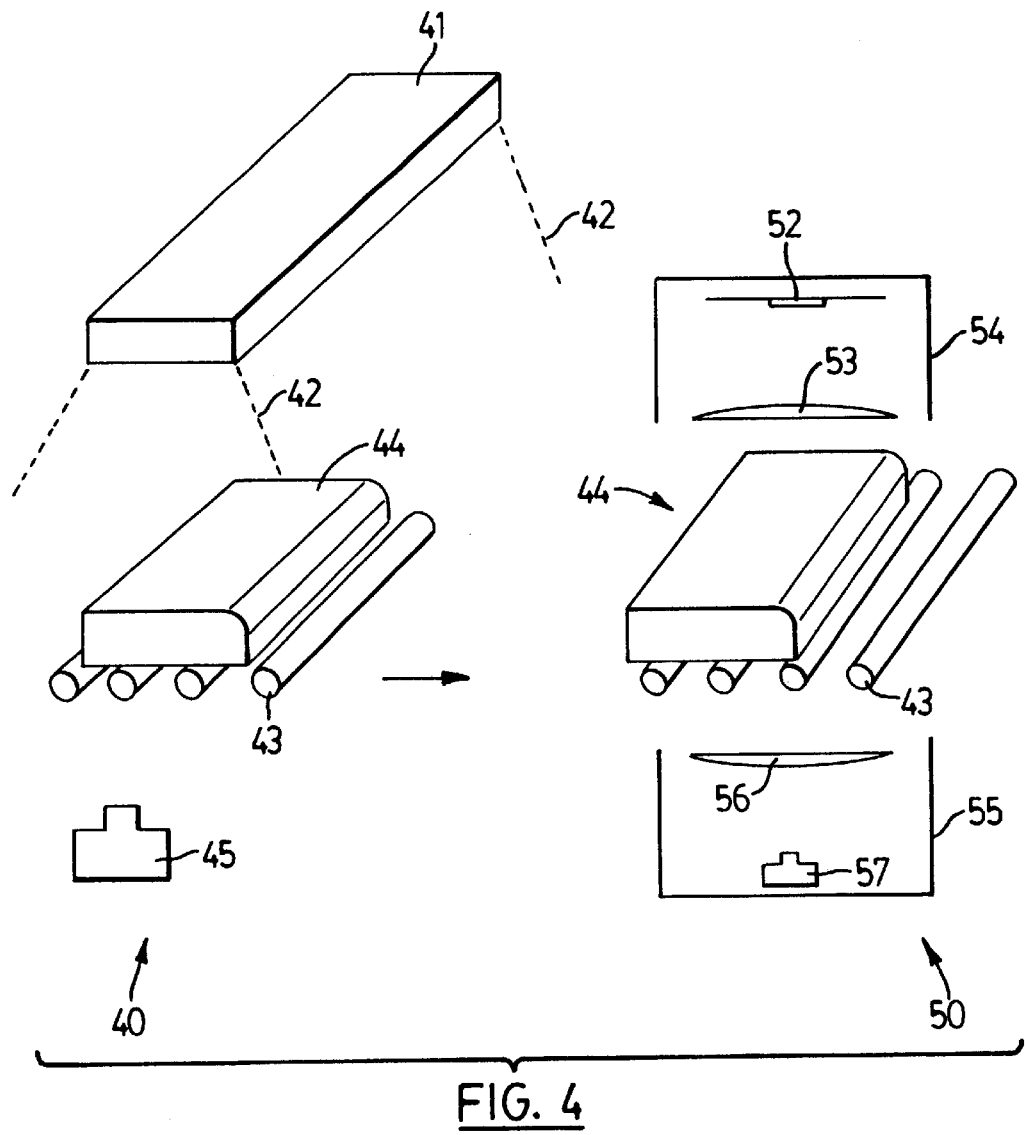
FIG. 4 is a schematic representation of a viewing area inspection apparatus combined with a dark view inspection apparatus.

FIG. 4 shows a viewing area inspection system, generally indicated by 40, in-line with a dark view inspection apparatus, generally indicated by 50. Viewing area inspection system 40 has an illuminator 41, which preferably provides distributed illumination as indicated by 42. A series of rollers 43 are provided to move a transparent medium 44 through the viewing area inspection system. Transparent medium 44 is shown in the form of a face plate for a cathode ray tube (CRT) which is one preferred form of the transparent medium to be inspected. An optical recording device e.g. a camera, 45 is located beneath rollers 43 to record images from transparent medium 44. Lenses may be provided to assist in the focusing and directing of light to optical recording device 45. Optical recording device 45 would be focussed at the upper surface 46 of transparent medium 44.

FIG. 4 also shows dark view inspection system 50 which is preferably located in series with viewing area inspection system 40, and most preferably utilizes the same series of rollers 43 as viewing area inspection system. Continuous transportation of a transparent medium 44 is important so that the transparent medium 44 is in the same orientation in both inspection systems.

Dark view inspection system 50 has been described above. A light source 51 provides distributed illumination, expect at aperture stop 52. Light source 51, aperture stop 52 and first lens 53 are located in upper housing 54. Lower housing 55 has second lens 56 and optical recording device 57. Upper housing 54 and lower housing 55 are on opposed sides of rollers 43.

In operation, a transparent medium 44 is passed through viewing area inspection system 40 and then through dark view inspection system 50. Images of transparent medium 44 are recorded by optical recording devices 45 and 57. Maintaining the transparent medium 44 on the same rollers and in the same orientation permits combination of the images obtained by optical recording devices 45 and 57, to provide a composite image of transparent medium 44.

Figure 5:
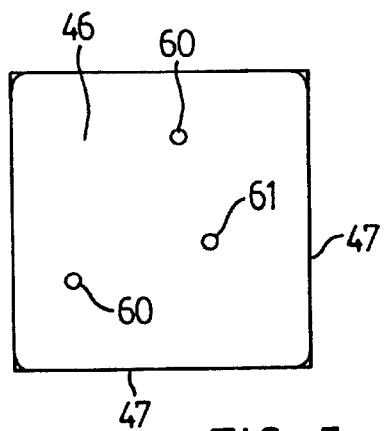
FIG. 5 is a schematic representation of a composite image generated by combining images captured by the apparatuses of FIG. 4.

An example of a composite image is shown in FIG. 5. The image is of upper surface 46 of transparent medium 44, with edges 47 of transparent medium 44 being shown. Edges 47 provide the reference points for locating of defects 60 and 61. Defect 60 is a light diverting and transparent defect with optical properties that would be observed by the dark view optical recording device 57. Such a defect might additionally be observed by the viewing area optical recording device 45. Defect 61 is an opaque defect e.g. a piece of solid matter such as a piece of sand, which would be observed and located by both optical recording device 45 and optical recording device 57.

The nature and characteristics of the images obtained by the optical recording devices, including whether defects are observed by one or both optical recording devices, provides information on the type and source of the defects. Such information assists in determining whether the transparent medium meets specifications, assists in classification of the defects and assists in identifying the source and causes of the defects.

Both optical recording devices would be connected to a computer having software to record and analyze the images received, and with information on the rate of movement of the transparent medium, to coordinate and combine the image. Analysis of images has been discussed above.

A variety of viewing area inspection systems may be used. For instance, if the transparent medium was a flat sheet of transparent medium, the viewing area inspection system could be the inspection system of Adam Weiss and Alexandre Obotnine disclosed in Canadian patent application No. 2,252,308 filed Oct. 30, 1998, which utilizes lasers instead of distributed illumination.

The present invention provides a versatile apparatus and method for inspection of transparent media, and which is capable of simultaneously identifying a wide variety of defects by type, magnitude and location, in a manner that not only permits identification of transparent media that does not meet product specifications but also assists in identifying the causes of the defects.

What is claimed is:

1. Apparatus for the detection and identification of light diverting and transparent defects with optical properties in a transparent medium, comprising:
   a circularly symmetrical illumination source including a light source of extended length and width and a circular aperture stop located at said light source;
   a lens system to form a column of circularly symmetrical light from light provided by said illumination source and to focus said column of circularly symmetrical light and an image of said aperture stop at a plane;
   an optical recording device located at said and aperture stop image; and
   means to pass said transparent medium through said column of circularly symmetrical light.

2. The apparatus of claim 1 in which the lens system comprises a first lens to form said column of light and a second lens to focus said column of light at said plane, said means to pass the transparent medium causing said transparent medium to pass between said first and second lens.

3. The apparatus of claim 2 in which the system additionally comprises a computer communicating with said optical recording device, said computer executing software to determine the location, type and magnitude of light diverting and transparent defects with optical properties in the sheet of transparent medium based on image data generated by said optical recording device.

4. The apparatus of claim 3 in which the computer includes a monitor and wherein said software generates a defect map showing the location, type and magnitude of defects in the transparent medium for display on said monitor.

5. The apparatus of claim 3 in which detection and identification includes a measurement of size.

6. The apparatus of claim 1 in which the light source is a diffused light source.

7. The apparatus of claim 6 in which the aperture stop is on said diffused light source.

8. The apparatus of claim 6 in which the aperture stop is spaced from said diffused light source.

9. The apparatus of claim 6 wherein said aperture stop is circular.

10. The apparatus of claim 1 in which the transparent medium is glass.

11. The apparatus of claim 1 in which the transparent medium is plastic.

12. The apparatus of claim 1 in which the lens system includes a mirror to reflect said light to said optical recording device.

13. A method for detection and identification of light diverting and transparent defects with optical properties in a transparent medium, comprising:
   a) passing said transparent medium through a column of circularly symmetrical light provided by a circularly symmetrical illumination source including a source of light and a circular aperture stop;
   b) focusing said column of circularly symmetrical light at a plane, an image of said aperture stop also being focused at said plane; and
   c) recording light diverted by a light diverting and transparent defect with optical properties in said transparent medium using an optical recording device positioned at said aperture stop image.

14. The method of claim 13 in which said recording of diverted light is analysed using computer software.

15. The method of claim 14 in which said software determines the location, type and magnitude of light diverting and transparent defects with optical properties in the transparent medium.

16. The method of claim 15 in which defects having a size down to 3 microns are detected.

17. The method of claim 15 in which the transparent medium is flat glass.

18. The method of claim 15 in which the transparent medium is curved glass.

19. The method of claim 15 in which the transparent medium is formed of glass.

20. The method of claim 15 in which the transparent medium is plastic.

21. The method of claim 15 in which the transparent medium is the face plate of a cathode ray tube.

22. The method of claim 15 in which detection and identification includes a measurement of size.

23. Apparatus for the detection and identification of light diverting and transparent defects with optical properties in a transparent medium, comprising:
   a) first and second illumination sources of extended length and width, each illumination source providing a column of light, said second illumination source including a light source and a circular aperture stop located at said light source, the column of light provided by said second illumination source being circularly symmetrical;
   b) a first optical recording device associated with the first illumination source and a second optical recording device associated with the second illumination source;
   c) means to pass said transparent medium through each column of light; and
   d) a lens system to focus the column of circularly symmetrical light provided by said second illumination source at a plane, an image of said aperture stop also being focused at said plane, said second optical recording device being located at said aperture stop image.

24. The apparatus of claim 23 in which the system additionally comprises a computer communicating with said optical recording device, said computer executing software to determine the location, type and magnitude of light diverting and transparent defects with optical properties in the sheet of transparent medium based on image data generated by said optical recording device.

25. The apparatus of claim 24 in which the computer includes a monitor and wherein said software generates a defect map showing the location, type and magnitude of defects in the transparent medium for display on said monitor.

26. A method for the detection and identification of defects in a transparent medium, comprising:
 a) passing said transparent medium through first and second columns of light, one of said columns of light being circularly symmetrical;
 b) focusing the first column of light at a first optical recording device and focusing the second column of light at a second optical recording device;
 c) recording images of said transparent medium at said first and second optical recording devices; and
 d) combining said images for detection and identification of the defects.

27. The method of claim 26 in which the defects include light diverting and transparent defects with optical properties.

28. The method of claim 27 in which the images are analyzed using computer software.

29. The method of claim 28 in which said software determines the location, type and magnitude of light diverting and transparent defects with optical properties in the transparent medium.

30. The method of claim 29 in which defects having a size down to 3 microns are detected.

31. The method of claim 29 in which the transparent medium is flat glass.

32. The method of claim 29 in which the transparent medium is curved glass.

33. The method of claim 29 in which the transparent medium is formed of glass.

34. The method of claim 29 in which the transparent medium is plastic.

35. The method of claim 29 in which the transparent medium is the face plate of a cathode ray tube.

36. The method of claim 29 in which detection and identification includes a measurement of size.

37. An apparatus for detecting defects in a transparent medium comprising:
 a circularly symmetrical diffused illumination source including a light source and a circular aperture stop, said illumination source providing a generally even distribution of light;
 a lens system forming a column of circularly symmetrical light from said even distribution of light and focusing said column of circularly symmetrical light as well as an aperture stop image at a plane;
 an optical recording device located at said aperture stop image; and
 a conveyor passing a transparent medium through said column of circularly symmetrical light, said optical recording device capturing images of defects in said transparent medium as a result of light beams in said column of circularly symmetrical light diverted by said defects.

38. The apparatus of claim 37 wherein said aperture stop is located on said light source.

39. The apparatus of claim 38 wherein said lens system includes a first lens assembly forming said column of light and a second lens assembly focusing said column of light at said plane, said conveyor passing said transparent medium between said first lens assembly and said second lens assembly.

40. The apparatus of claim 39 further comprising a mirror disposal between said second lens assembly and said optical recording device to reflect the focused column of light at said plane.

41. The apparatus of claim 40 wherein said plane is generally parallel with said column of light formed by said first lens assembly.

42. The apparatus of claim 39 further comprising a housing through which said conveyor passes, said housing accommodating said illumination source, said lens system and said optical recording device and being pressurized to inhibit dust from entering said housing.

43. The apparatus of claim 42 wherein said housing includes an upper housing above said conveyor accommodating said illumination source and said first lens assembly and a lower housing below said conveyor accommodating said second lens assembly and said optical recording device.

44. The apparatus of claim 42 wherein said optical recording device is a line-scan camera.

45. The apparatus of claim 42 further comprising a processor in communication with said optical recording device, said processor processing image data generated by said optical recording device to determine the type and nature of said defects.

46. The apparatus of claim 45 wherein processed image data is displayed on a computer monitor as a map showing detected defects.

47. The apparatus of claim 46 wherein said detected defects are displayed on said map as icons, the shapes of said icons representing the types of the detected defects.

48. The apparatus of claim 45 in combination with a viewing area inspection apparatus, said viewing area inspection apparatus capturing an image of said transparent medium, the image generated by said viewing area inspection apparatus being combined with images captured by said optical recording device to generate a composite image of said transparent medium.

49. An apparatus for detecting defects in a transparent medium comprising:
 a circularly symmetrical diffused illumination source including a light source and a plurality of circular aperture stops at spaced locations relative to said light source, said illumination source providing a generally even distribution of light;
 a lens system forming a column of circularly symmetrical light from said even distribution of light and focusing said column of circularly symmetrical light as well as aperture stop images at a plane;
 an optical recording device located at each said aperture stop image; and
 a conveyor passing a transparent medium through said column of light, each said optical recording device capturing images of defects in said transparent mediums as a result of light beams in said column of light diverted by said defects.

50. The apparatus of claim 49 wherein said aperture stops are located on said light source.

51. The apparatus of claim 50 wherein said lens system includes a first lens assembly forming said column of light and a second lens assembly focusing said column of light at said plane, said conveyor passing said transparent medium between said first lens assembly and said second Tens assembly.

52. The apparatus of claim 51 comprising a mirror disposal between said second lens assembly and said optical recording device to reflect the focused column of light at said plane.

53. The apparatus of claim 52 wherein said plane is generally parallel with said column of light formed by said first lens assembly.

54. The apparatus of claim 51 further comprising a housing through which said conveyor passes said housing accommodating said illumination source, said lens system and said optical recording devices and being pressurized to inhibit dust from entering said housing.

55. The apparatus of claim 54 wherein said housing includes an upper housing above said conveyor accommodating said illumination source and said first lens assembly and a lower housing below said conveyor accommodating said second lens assembly and said optical recording devices.

56. The apparatus of claim 55 wherein said optical recording devices are line-scan cameras.

57. The apparatus of claim 56 further comprising a processor in communication with said optical recording devices, said processor processing image data generated by said optical recording devices to determine the type and nature of said defects.

* * * * *